United States Patent
Gelbart

(10) Patent No.: US 9,991,014 B1
(45) Date of Patent: Jun. 5, 2018

(54) FAST POSITIONABLE X-RAY FILTER

(71) Applicant: Daniel Gelbart, Vancouver (CA)

(72) Inventor: Daniel Gelbart, Vancouver (CA)

(*) Notice: Subject to any disclaimer, the term of this patent is extended or adjusted under 35 U.S.C. 154(b) by 74 days.

(21) Appl. No.: 14/862,131

(22) Filed: Sep. 22, 2015

Related U.S. Application Data

(60) Provisional application No. 62/054,374, filed on Sep. 23, 2014.

(51) Int. Cl.
  *G21K 1/02* (2006.01)
  *G21K 1/04* (2006.01)
  *A61B 6/06* (2006.01)

(52) U.S. Cl.
  CPC .............. *G21K 1/043* (2013.01); *A61B 6/06* (2013.01); *G21K 1/02* (2013.01); *G21K 1/025* (2013.01); *G21K 1/04* (2013.01)

(58) Field of Classification Search
  CPC . G21K 1/10; G21K 1/02; G21K 1/025; A61B 6/032; A61B 6/035; A61B 6/4035; A61B 6/4042; A61B 6/482
  USPC ... 378/5, 16, 98.9, 98.11, 156–159, 62, 148, 378/149
  See application file for complete search history.

(56) References Cited

U.S. PATENT DOCUMENTS

| | | | | |
|---|---|---|---|---|
| 4,277,685 A | * | 7/1981 | Covic | G03B 42/02 378/150 |
| 4,399,550 A | * | 8/1983 | Hauck | A61B 6/06 378/157 |
| 4,489,426 A | | 12/1984 | Grass | |
| 4,686,695 A | * | 8/1987 | Macovski | A61B 6/032 348/E5.089 |
| 4,744,099 A | * | 5/1988 | Huettenrauch | A61B 6/0414 378/156 |
| 4,859,849 A | * | 8/1989 | Shimura | G03B 42/02 250/582 |
| 4,868,843 A | | 9/1989 | Nunan | |
| 4,896,037 A | * | 1/1990 | Shimura | G03B 42/021 250/583 |
| 4,969,174 A | * | 11/1990 | Scheid | A61B 6/502 378/146 |
| 5,081,660 A | * | 1/1992 | Fujisaki | G03B 42/02 348/E5.086 |

(Continued)

OTHER PUBLICATIONS

Abhinav Bal ; Normand Robert ; Lindsay Machan ; Meir Deutsch ; David Kisselgoff ; Paul Babyn ; John A. Rowlands; Order of magnitude reduction of fluoroscopic x-ray dose. Proc. SPIE 8313, Medical Imaging 2012: Physics of Medical Imaging, 831356 (Feb. 23, 2012).

*Primary Examiner* — Allen C. Ho

(57) ABSTRACT

The preferred embodiment of the disclosed invention comprises rotary actuators that move one or more x-ray attenuating plates in the x-y plane (ie. image plane). These x-ray attenuating plates attenuate the x-ray beam with thin metal sheets or plates that contain one or more apertures, which fully exposes the desired region of interest (ROI) while filtering the rest of the image, reducing the radiation exposure for the procedure. The devices will typically have a selection of many attenuation profiles. A small aperture or low attenuation profile region will result in a higher total exposure reduction and a large aperture or large attenuation profile will result in a smaller exposure reduction. The x-ray attenuating plate can be rotated to select an attenuation profile using a detent wheel.

6 Claims, 2 Drawing Sheets

(56) References Cited

U.S. PATENT DOCUMENTS

| | | | | |
|---|---|---|---|---|
| 5,107,529 A | * | 4/1992 | Boone | A61B 6/4035 359/890 |
| 5,131,022 A | * | 7/1992 | Terashima | G03F 7/2008 250/492.2 |
| 5,204,888 A | * | 4/1993 | Tamegai | A61B 6/4035 378/156 |
| 5,278,887 A | | 1/1994 | Chiu | |
| 5,282,254 A | * | 1/1994 | Chiu | A61B 6/06 378/159 |
| 5,369,678 A | * | 11/1994 | Chiu | A61B 6/542 378/152 |
| 5,396,532 A | * | 3/1995 | Aichinger | A61B 6/502 378/108 |
| 5,396,889 A | * | 3/1995 | Ueda | A61B 6/032 250/363.1 |
| 5,568,533 A | * | 10/1996 | Kumazaki | G21K 1/04 378/156 |
| 5,572,037 A | * | 11/1996 | Liu | G01N 23/043 250/363.02 |
| 5,661,774 A | * | 8/1997 | Gordon | G01N 23/046 378/101 |
| 5,680,434 A | * | 10/1997 | Thelosen | A61B 6/06 378/150 |
| 5,689,544 A | * | 11/1997 | Van Den Besselaar | A61B 6/06 378/150 |
| 5,881,127 A | | 3/1999 | Molloi | |
| 5,991,362 A | * | 11/1999 | Jones | G21K 1/04 378/150 |
| 6,036,362 A | * | 3/2000 | Schmitt | A61B 6/08 378/150 |
| 6,094,474 A | * | 7/2000 | Vezina | G21K 1/10 378/156 |
| 6,118,848 A | * | 9/2000 | Reiffel | A61N 5/1049 378/162 |
| 6,148,062 A | * | 11/2000 | Romeas | G21K 1/10 378/156 |
| 6,226,352 B1 | * | 5/2001 | Salb | A61B 6/4035 378/143 |
| 6,301,334 B1 | * | 10/2001 | Tybinkowski | A61B 6/06 378/147 |
| 6,389,108 B1 | * | 5/2002 | Ein-Gal | G21K 1/04 250/505.1 |
| 6,396,902 B2 | * | 5/2002 | Tybinkowski | G21K 1/025 378/148 |
| 6,501,828 B1 | * | 12/2002 | Popescu | A61B 6/06 378/145 |
| 6,597,758 B1 | * | 7/2003 | Rosner | G01N 23/04 378/156 |
| 6,614,878 B2 | * | 9/2003 | Bogatu | A61B 6/4042 378/156 |
| 6,633,627 B2 | * | 10/2003 | Horiuchi | A61B 6/032 378/156 |
| 6,851,854 B2 | * | 2/2005 | Schmitt | A61B 6/06 250/252.1 |
| 7,050,544 B2 | * | 5/2006 | Karlsson | A61B 6/502 378/148 |
| 7,092,490 B2 | * | 8/2006 | Saladin | A61B 6/4035 356/418 |
| 7,120,222 B2 | * | 10/2006 | Hoffman | A61B 6/032 378/124 |
| 7,132,674 B2 | * | 11/2006 | Pastyr | G21K 1/04 250/505.1 |
| 7,254,216 B2 | * | 8/2007 | Thandiackal | A61B 6/032 378/157 |
| 7,263,171 B2 | * | 8/2007 | Zhang | G21K 1/04 250/505.1 |
| 7,330,535 B2 | * | 2/2008 | Arenson | G21K 1/04 378/156 |
| 7,343,003 B2 | * | 3/2008 | Li | G21K 1/04 250/505.1 |
| 7,380,986 B2 | * | 6/2008 | Brandstatter | A61B 6/08 378/206 |
| 7,386,097 B2 | * | 6/2008 | Kerpershoek | G01N 23/20008 378/148 |
| 7,463,715 B2 | * | 12/2008 | Spahn | A61B 6/4035 378/114 |
| 7,483,518 B2 | * | 1/2009 | Hamill | G21K 1/10 378/119 |
| 7,508,918 B2 | * | 3/2009 | Liu | G21K 1/04 378/147 |
| 7,539,284 B2 | | 5/2009 | Besson | |
| 7,636,413 B2 | * | 12/2009 | Toth | A61B 6/032 378/157 |
| 7,649,981 B2 | * | 1/2010 | Seppi | A61B 6/032 378/124 |
| 7,680,249 B2 | * | 3/2010 | Yuan | A61B 6/00 378/156 |
| 7,723,690 B2 | * | 5/2010 | Uribe | A61B 6/032 250/363.02 |
| 7,742,568 B2 | * | 6/2010 | Smith | G01N 23/087 378/57 |
| 7,783,007 B2 | * | 8/2010 | Echner | G21K 1/04 378/150 |
| 7,831,023 B2 | * | 11/2010 | Wedel | A61B 6/06 378/148 |
| 7,852,990 B2 | * | 12/2010 | Aulbach | G21K 1/04 378/148 |
| 7,869,862 B2 | * | 1/2011 | Seppi | A61B 6/032 600/420 |
| 7,983,388 B2 | * | 7/2011 | Michaelsen | G21K 1/04 378/145 |
| 7,983,391 B2 | * | 7/2011 | Machan | A61B 6/06 378/151 |
| 8,009,807 B2 | * | 8/2011 | Petrik | G21K 1/04 378/148 |
| 8,077,830 B2 | * | 12/2011 | Brown | A61N 5/1048 378/156 |
| 8,130,901 B2 | * | 3/2012 | Müller | A61B 6/06 378/147 |
| 8,284,903 B2 | * | 10/2012 | Yuan | A61B 6/06 378/156 |
| 8,445,878 B2 | * | 5/2013 | Guez | A44C 5/20 250/396 R |
| 8,565,378 B2 | * | 10/2013 | Echner | A61N 5/1042 378/148 |
| 8,571,178 B2 | * | 10/2013 | Sendai | A61B 6/4042 378/157 |
| 8,693,628 B2 | | 4/2014 | Machan | |
| 8,731,142 B2 | * | 5/2014 | Tanabe | G21K 1/046 250/505.1 |
| 8,824,638 B2 | * | 9/2014 | Nicholson | A61B 6/06 378/150 |
| 8,890,100 B2 | * | 11/2014 | Huntzinger | G21K 1/10 250/503.1 |
| 9,014,341 B2 | * | 4/2015 | Zhang | A61B 6/03 378/147 |
| 9,050,028 B2 | | 6/2015 | Guez | |
| 9,125,572 B2 | * | 9/2015 | Noo | A61B 6/027 |
| 9,254,109 B2 | * | 2/2016 | Becker | A61B 6/032 |
| 9,406,411 B2 | * | 8/2016 | Sayeh | G21K 1/04 |
| 9,480,443 B2 | * | 11/2016 | Feuerlein | A61B 6/032 |
| 9,504,439 B2 | * | 11/2016 | Yi | A61B 6/5205 |
| 9,592,014 B2 | * | 3/2017 | Melman | A61B 6/06 |
| 2014/0294146 A1 | | 10/2014 | Guez | |
| 2015/0023466 A1 | | 1/2015 | Melman | |

* cited by examiner

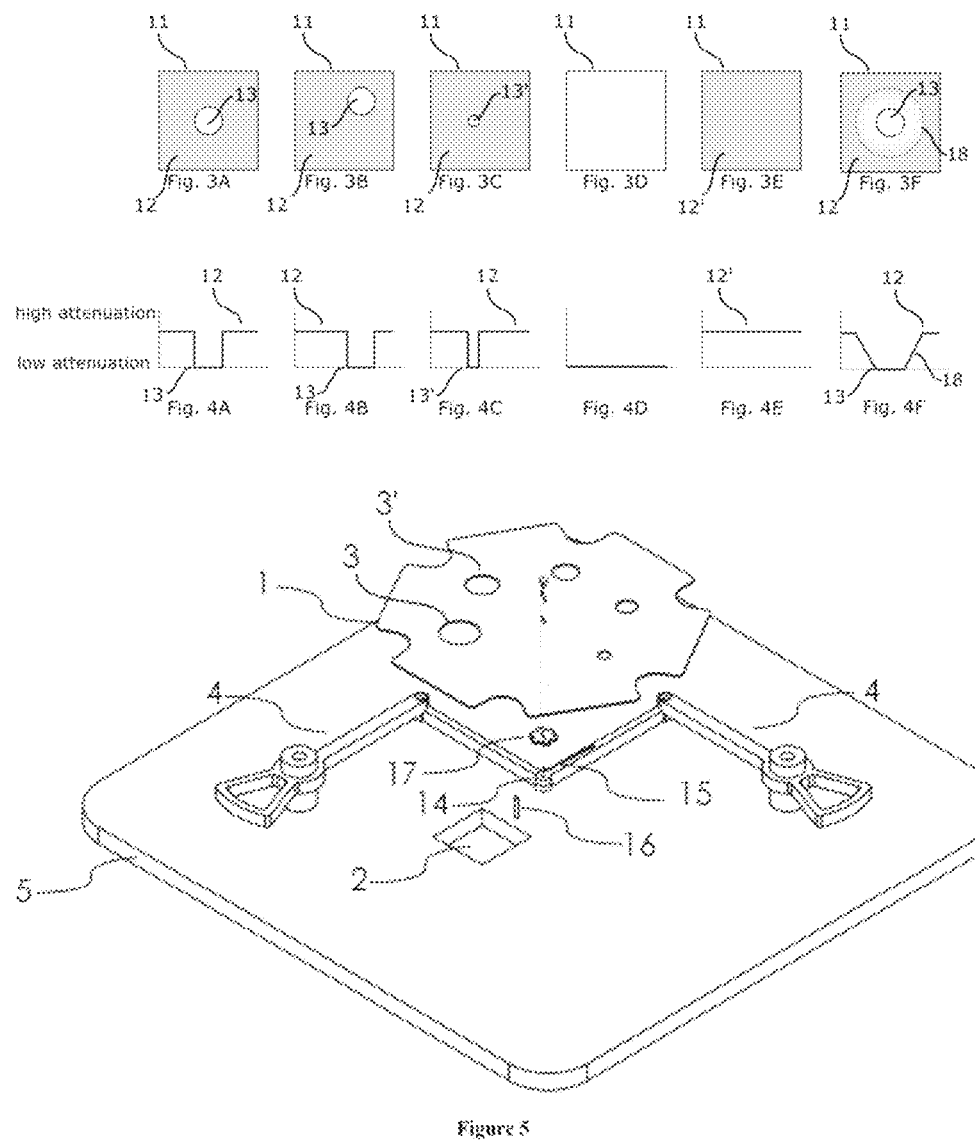

FAST POSITIONABLE X-RAY FILTER

FIELD OF THE INVENTION

The invention is in the medical field, in particular in X-Ray dose reduction.

BACKGROUND OF THE INVENTION

X-Ray imaging is important for diagnostic and interventional procedures, but comes with many risks to the patient and staff. The medical industry is striving to find solutions to minimize radiation exposure during such procedures. One of the best ways to minimize the radiation exposure is to filter the x-ray beam outside of the region of interest (ROI). X-Ray attenuation filters are usually made of thin metal plates, such as lead, steel or aluminum.

Salient features such as anatomical features or tool tips will move during any procedure. If the filtering mechanism has a static aperture, the user requires a longer exposure to reposition the patient table.

An x-ray image benefits from high levels of radiation exposure for several reasons. High energy level x-ray beams are less likely to be attenuated by hard tissue, allowing tissue such as bone to be imaged. A higher X-ray beam energy greatly reduces signal-to-noise ratio in low exposure images. The contrast and image exposure is also reduced in low energy x-ray images, making it difficult to discern features. Background regions, ie. regions that do not contain salient features, do not need to have the same image quality and, therefore, the user can sacrifice the image quality to reduce their exposure to harmful ionizing radiation.

There are three types of x-ray attenuation devices that are designed to select an area of interest. The first type has a continuously variable attenuation profile with a continuously variable position. An example of this method is demonstrated in U.S. Pat. No. 8,693,628. This type is typically expensive to build and requires many heavy moving parts. The second type has a fixed size with a variable position, such as U.S. Pat. No. 5,278,887 and US Application 2015/0023466. This second type cannot typically be adjusted in terms of shape and size, limiting the ability of these devices to reduce radiation exposure. The third type has a variable aperture size, but cannot vary the position. These are the most common types of collimators and attenuation devices, examples are U.S. Pat. Nos. 5,881,127, 4,868,843 and 4,489,426. All three types typically limit the user to one aperture shape, such as a rectangle or a circle.

The disclosed invention a method of reducing radiation exposure using a set of fixed of apertures or filters with varying attenuation profiles. The preferred embodiment selects one of the fixed apertures or filters and positions it in the image area using rotary actuators. This method provides the flexibility of multiple attenuation profile shapes and sizes, while also allowing the user to position the attenuation profile around an area of interest. Another advantage of this invention is that the mechanism is sufficiently fast enough to repeatedly change position and attenuation profiles within one medical procedure, which is typically not possible with modern collimators, such as the type three devices described above.

SUMMARY OF THE INVENTION

The preferred embodiment of the disclosed invention comprises rotary actuators that move one or more x-ray attenuating plates in the x-y plane (ie. image plane). These plates attenuate the x-ray beam with thin metal sheets or plates that contain one or more apertures, which fully exposes the desired ROI while filtering the rest of the image, reducing the radiation exposure for the procedure. The devices will typically have a selection of many attenuation profiles. A small aperture or low attenuation profile region will result in a higher total exposure reduction and a large aperture or large attenuation profile will result in a smaller exposure reduction. The x-ray attenuating plate can be rotated to select an attenuation profile using a detent wheel.

DESCRIPTION OF DRAWINGS

FIGS. 3A through 4F are image layouts that can be acquired using the device.

FIGS. 4A through 4F are plots showing example attenuation profiles.

FIG. 5 is an exploded view of the selection mechanism in the apparatus.

DETAILED DESCRIPTION

Figure 1:
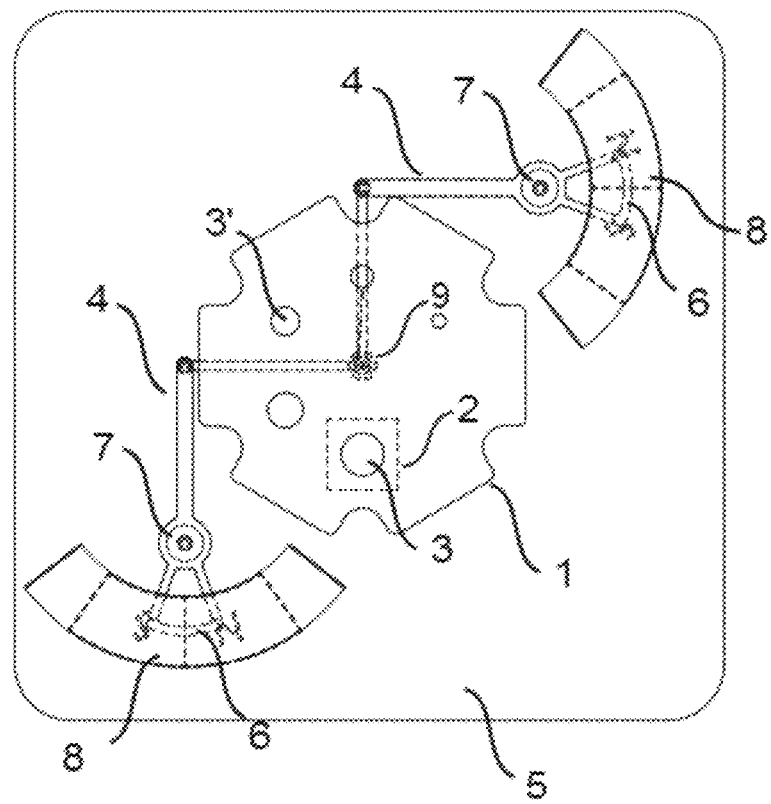
FIG. 1 is a schematic description of the preferred embodiment.

Referring to FIG. 1, the X-ray beam attenuation is controlled by one or more X-ray attenuating plates 1 in the direct path of the X-ray beam in the field of view 2. The preferred embodiment of the X-ray attenuating plate 1 has at least one hole 3 that allows the X-ray beam to pass through the metal encasement 5 without attenuating or less attenuation that the surrounding areas. This X-ray attenuating plate 1 has creates attenuation profiles that can be used to selectively filter regions that contain little interesting or salient features, while maintaining high image quality in the ROI. An attenuation profile is a feature of the X-ray device which provides different levels of filtering that may vary in within the field of view 2 of an X-ray device. As the total X-ray attenuation in an attenuation profile increases, the radiation exposure decreases. In the preferred embodiment, X-ray attenuating plate 1 comprises a set of fixed attenuation profiles, one of which is selected and positioned over the field of view 2 at any given time during operation. FIG. 1 depicts the X-ray attenuating plate 1 as a solid piece of thin metal, but it is possible that it is made of several components. The entire X-ray attenuating plate 1 can be removed by over-extending arms 4 away from the field of view 2 in metal encasement 5, which allows the entire image to be unattenuated. Rotary actuators are used to move the over-extending arms 4 and position the hole 3. The actuator comprises a over-extending arm 4 carrying a coil 6 rotating on bearing 7. The torque rotating the over-extending arms 4 is created by the interaction of the electric current in coil 6 with the magnetic field of magnets 8. The attenuation profile can be selected by rotating the X-ray attenuating plate 1 using a detent wheel 9. This configuration is very fast and can be used to select, position and/or remove an attenuation profile between X-ray pulses; often a time span of less than 20 ms. This allows the attenuation profile to appear stationary for each image, but move and potentially track an area-of-interest over time.

There are foreseeable circumstances where the user may want the x-ray attenuating plate 1 to move during an x-ray pulse, ie. while an image is being captured. This could be used, for example, to create a supplementary attenuation profile that is dependent on time and position as well as the fixed profile provided by x-ray attenuating plate 1.

Figure 2:
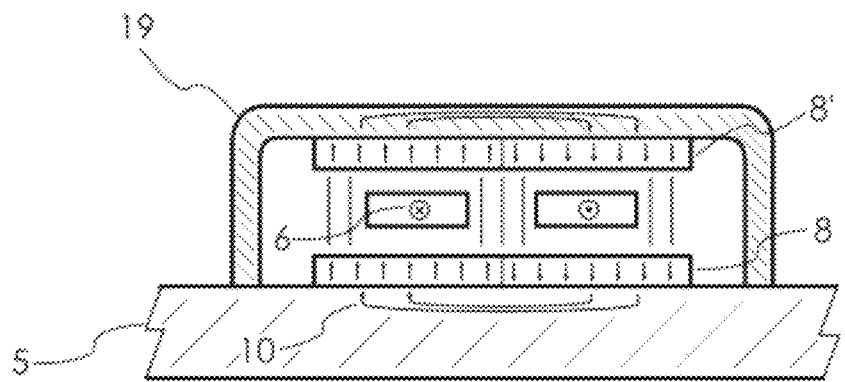
FIG. 2 shows the magnetic circuit that drives the device.

The magnetic circuit of the actuator is shown in FIG. 2. The magnetic path is completed by the metal encasement 5, made of steel, and top plate 19, also made of steel. The magnetic design shown in FIG. 2 is well known as it is used in computer hard-drives. The magnetization of magnets 8 and 8' reverses in the middle of the magnet in order to keep the force on both parts of coil 6 acting in the same direction. The magnetic flux is shown by 10.

FIGS. 3A-F show the possible image 11 configurations resulting from an X-ray exposure using the disclosed x-ray device. The grey regions indicate the X-ray beam was attenuated by the X-ray attenuating plate 1 in said grey regions. The preferred usage of the disclosed invention is exemplified in FIG. 3F. In each of these images, the image 11 comprises a background 12 (the area exposed to X-ray beam attenuated by X-ray attenuating plate 1), and a ROI 13 (the area in an image that is either attenuated with a hole 3 in X-ray attenuating plate 1 or the area in an image 11, where the X-ray beam passes through a hole 3). FIGS. 3B and 3C show the image 11 can be modified by changing the x-y position of the X-ray attenuating plate 1 or rotating the X-ray attenuating plate 1 to select another hole 3 respectively. Rotating the X-ray attenuating plate 1 results in an images such as FIG. 3C, where ROI 13' is a different size. There are circumstances that the user would remove the x-ray attenuating plate 1, FIG. 3D, to expose the entire field of view 2 without attenuating the X-ray beam. Similarly, the user may select a region of X-ray attenuating plate 1 that does not contain any hole 3, and therefore filter the entire field of view 2 of the X-ray beam, FIG. 3E. FIG. 3F depicts a non-uniform attenuation profile surrounding the hole 3 or background 12 of low attenuation. The tapering attenuation region 18 has a decreasing attenuation as it approaches the ROI 13. The tapering attenuation in region 18 can be accomplished with decreasing the thickness of X-ray attenuating plate 1 as it approaches the ROI 13, for example. In the preferred embodiment, ROI 13 is typically made by cutting a hole 3 in X-ray attenuating plate 1 to form an aperture, however other ways to create ROI 13 are by incorporating a second material with a lower attenuation characteristic or carrying the thickness of the X-ray attenuating plate 1.

FIGS. 4 A-F are graphs that depict attenuation profiles that correspond to FIGS. 3 A-F, respectively. In FIGS. 4 A-C, high attenuating areas comprise the background 12 and low attenuating areas encompass the ROIs 13 and 13'. FIG. 4 D is the attenuation profile with the x-ray attenuating plate 1 out of the image 11 and FIG. 4E is the attenuation profile with a uniform x-ray attenuating plate 1 in the image 11. FIG. 4 F is an example of a non-binary or non-uniform attenuation profile with a tapering attenuation region 18 near the ROI 13.

It is foreseeable that other configurations can be used to create an attenuation profile, and this disclosure covers all possibilities of such configurations. Some examples of other configurations are that can be used to create attenuation profiles:
1. Non-circular holes 3.
2. Multiple holes 3 that are present in the field of view 2.
3. Variable plate thickness resulting in non-uniform attenuation, with or without holes 3. An example is a wedge filter, where the attenuation decreases towards a hole 3.
4. Multiple overlapping x-ray attenuating plates 1.
5. X-ray attenuating plates 1 with multiple materials with varying attenuation characteristics.
6. Uniform attenuation profile without a hole 3. This may simply be a uniform region of x-ray attenuating plate 1 or a region of x-ray attenuating plate 1 that is uniformly thicker or thinner to create a filter with a uniform attenuation at a higher or lower level.
7. Non-uniform attenuation profile without a hole 3. In this embodiment, the ROI 13 would be aligned with the lower attenuating regions of the attenuation profile.

The hole selection mechanism in the preferred embodiment is show in FIG. 5. The selection mechanism comprises the X-ray attenuating plate 1, a selected hole 3 and one or more inactive holes 3'. The X-ray-attenuating plate 1 is fixed to a detent wheel 9 which is held in an x-y position with over-extending arms 4. The detent wheel 9 can spin freely in joint 14 and is held in place during normal operation with detent spring 15. The X-ray attenuating plate 1 is rotated by over-extending arm 4 towards the fixed pin 16, such that fixed pin 16 connects with groove 17 and forces detent wheel 9 to rotate. The detent wheel 9 and X-ray attenuating plate 1 rotate until detent spring 15 latches with the desired groove 17, holding the detent wheel 9 in position. It can be foreseen that the desired holes 3 or X-ray attenuating plates 1 may be switched with a different selection mechanism. This invention covers such alternative configurations. The different attenuators are compensated by electronic processing, typically by adding gain to the attenuated image areas.

Note that we refer to the attenuator as a "thin metal plate", however, the attenuator can be made of many different materials and is not limited to one material or configuration. In the preferred embodiment, the x-ray attenuating plate 1 is made of a material which partially attenuates or absorbs an X-ray beam. Copper or titanium are example materials that commonly used to filter or partially attenuate an X-ray beam. A more radio-opaque material, such as lead, could also be used. In some modes of operation, the x-ray device has one or more x-ray attenuating plates 1, such as lead, that can be moved out of the field of view 2 at high speeds, similar to our previous patents (U.S. Pat. No. 7,983,391 and U.S. patent application Ser. No. 13/986,157), effectively creating a dual-mode x-ray attenuating shutter.

There are two methods to determine the x-y position of the hole 3. First, angular position sensors can be used on the rotary actuators, and the x-y coordinate of the over-extending arm 4 end can be calculated from this measurement. Since the two over-extending arms 4 are connected at the distal ends, a unique solution can be found. Another option is to measure the x-y position directly by installing an x-y position sensor on the x-ray attenuating plate 1. Such sensing technology is well known; an example an absolute optical linear encoder sensing the position of an optical scale or grating. This can be either a transparent or reflective optical scale.

The exposure reduction is depended on the size of hole 3 and the thickness of x-ray attenuating plate 1. Typical use of the disclosed x-ray device will result in about 60% exposure reduction, however, it is reasonable to see exposure reductions as high as 80%. Removal of the x-ray attenuating plate 1 from the field of view 2 would result in 0% exposure reduction.

A material that has a higher attenuation will reduce or absorb more of an X-ray beam than a material with a lower attenuation.

The preferred embodiment of the invention can operate without rotating the attenuation profile and hole 3, however, in cases where a different rotational configuration is desired, the detent wheel 9 can be used to rotate said attenuation profile and the actuators can move the attenuation profile in the field of view 2. The angular resolution of the attenuation profile is dependent on the number of grooves 17 on the detent wheel 9.

The selected attenuation profile and position of said profile can be determined by a user interface such as a touch screen or joystick. Automatic tracking can also be used to determine the position and shape/size of the attenuation profile. This can be done, for example, by tracking a tool tip. Methods of tracking are well known in industry. Examples given are U.S. Pat. No. 5,278,887 (Chiu) and U.S. Pat. No. 8,693,628 (Machan), both of which are incorporated by reference.

Definitions of terms used in this specification:

We typically refer to projection of the area of the image on to the device plane as the image area or field of view 2.

The term attenuation and absorption both refer to a material property that results in a reduction of intensity when an x-ray beam passes through it. When we refer to low attenuation, this could mean also mean negligible or no attenuation.

Tracking can refer to either manual selection and positioning of the attenuation profile or automatic methods that use user sensors or image processing techniques.

Region-of-interest and area-of-interest can be used interchangeably.

The invention claimed is:

1. An X-ray dose reduction device comprising:
   a plurality of rotary electromagnetic actuators; and
   a set of fixed attenuation profiles;
   wherein said plurality of rotary electromagnetic actuators select and position one or more of said set of fixed attenuation profiles anywhere in an image area.

2. A method for reducing a radiation level used when an X-ray image is created, said method comprising the steps of:
   selecting an area-of-interest in said X-ray image;
   exposing said area-of-interest using a fixed attenuation profile;
   wherein exposing said area-of-interest using a fixed attenuation profile comprises selecting said fixed attenuation profile from a set of fixed attenuation profiles using one or more rotary electromagnetic actuators;
   positioning said fixed attenuation profile such that a lowest attenuating region overlaps said area-of-interest using the one or more rotary electromagnetic actuators.

3. The method for reducing a radiation level used when an X-ray image is created as in claim 2, wherein selecting the fixed attenuation profile from a set of fixed attenuation profiles using one or more rotary electromagnetic actuators and positioning the fixed attenuation profile comprise selecting and positioning said fixed attenuation profile with the one or more rotary electromagnetic actuators.

4. The method for reducing a radiation level used when an X-ray image is created as in claim 2, wherein said fixed attenuation profile comprises at least one region that does not attenuate an X-ray beam.

5. The method for reducing a radiation level used when an X-ray image is created as in claim 2, wherein said fixed attenuation profile comprises a higher attenuating region and a lower attenuating region, and said lower attenuating region is at least as large as the area-of-interest.

6. The method for reducing a radiation level used when an X-ray image is created as in claim 2, wherein the area-of-interest is exposed using the fixed attenuation from a set of fixed attenuation profiles at a first refresh rate and said fixed attenuation profile from a set of fixed attenuation profiles is removed from the full image area at a second refresh rate slower than said first refresh rate.

* * * * *